United States Patent [19]

Ehnström

[11] 4,376,163
[45] Mar. 8, 1983

[54] PROCESS FOR PRODUCING ETHANOL BY CONTINUOUS FERMENTATION OF POLYSACCHARIDE-CONTAINING RAW MATERIALS

[75] Inventor: Lars K. J. Ehnström, Tullinge, Sweden

[73] Assignee: Alfa-Laval AB, Tumba, Sweden

[21] Appl. No.: 189,571

[22] Filed: Sep. 23, 1980

[30] Foreign Application Priority Data

Oct. 1, 1979 [SE] Sweden .............................. 79081055

[51] Int. Cl.³ .......................... C12P 7/06; C12P 7/10; C12P 7/14; C07C 31/08
[52] U.S. Cl. .................................... 435/162; 435/161; 435/165; 203/19
[58] Field of Search ............... 435/161, 162, 163, 813, 435/163, 164; 203/19; 426/7, 11, 13, 14

[56] References Cited

U.S. PATENT DOCUMENTS

| | | | |
|---|---|---|---|
| 385,625 | 5/1887 | Horne | 435/165 |
| 1,884,272 | 10/1932 | Sak | 435/256 |
| 1,921,991 | 11/1929 | Hildebrandt | 435/162 |
| 2,155,134 | 5/1937 | Karsch | 435/162 |
| 2,356,218 | 9/1941 | Christensen | 435/161 |
| 4,009,075 | 2/1977 | Hoge | 435/162 |
| 4,220,721 | 9/1980 | Emert et al. | 435/165 |

OTHER PUBLICATIONS

Cysewski et al., Biotechnology and Bioengineering, vol. XX, p. 1421–1444, 1968 (p. 1431–1435).

Primary Examiner—Raymond N. Jones
Assistant Examiner—John E. Tarcza
Attorney, Agent, or Firm—Davis, Hoxie, Faithfull & Hapgood

[57] ABSTRACT

This invention relates to a process for producing ethanol by continuous fermentation of polysaccharide-containing raw materials. The fermentation is carried out in one or several fermentors, a stream of fermentation liquor being separated into a yeast concentrate stream and a yeast-free stream, and possibly one sludge stream, of which the yeast concentrate stream is recirculated to the fermentor, at least part of the yeast-free stream being fed to a simple evaporator unit, corresponding to one or a few distilling stages, wherein it is separated, *partly* into a first vapor stream, enriched in ethanol, which is fed to a plant for production of the desired ethanol grade, and *partly* into a first liquid bottom stream, which is at least in part recirculated to the fermentor. Especially characterizing for the new process is, that a raw material stream is fed to a circulation circuit, comprising said fermentor and said evaporator unit, and that the raw material stream is hydrolyzed, in the evaporator unit, to a fermentable state. It is especially advantageous to carry out this hydrolysis by enzymes, preferably by a gluco-amylase at a temperature within the range 35° C. to 75° C.

15 Claims, 1 Drawing Figure

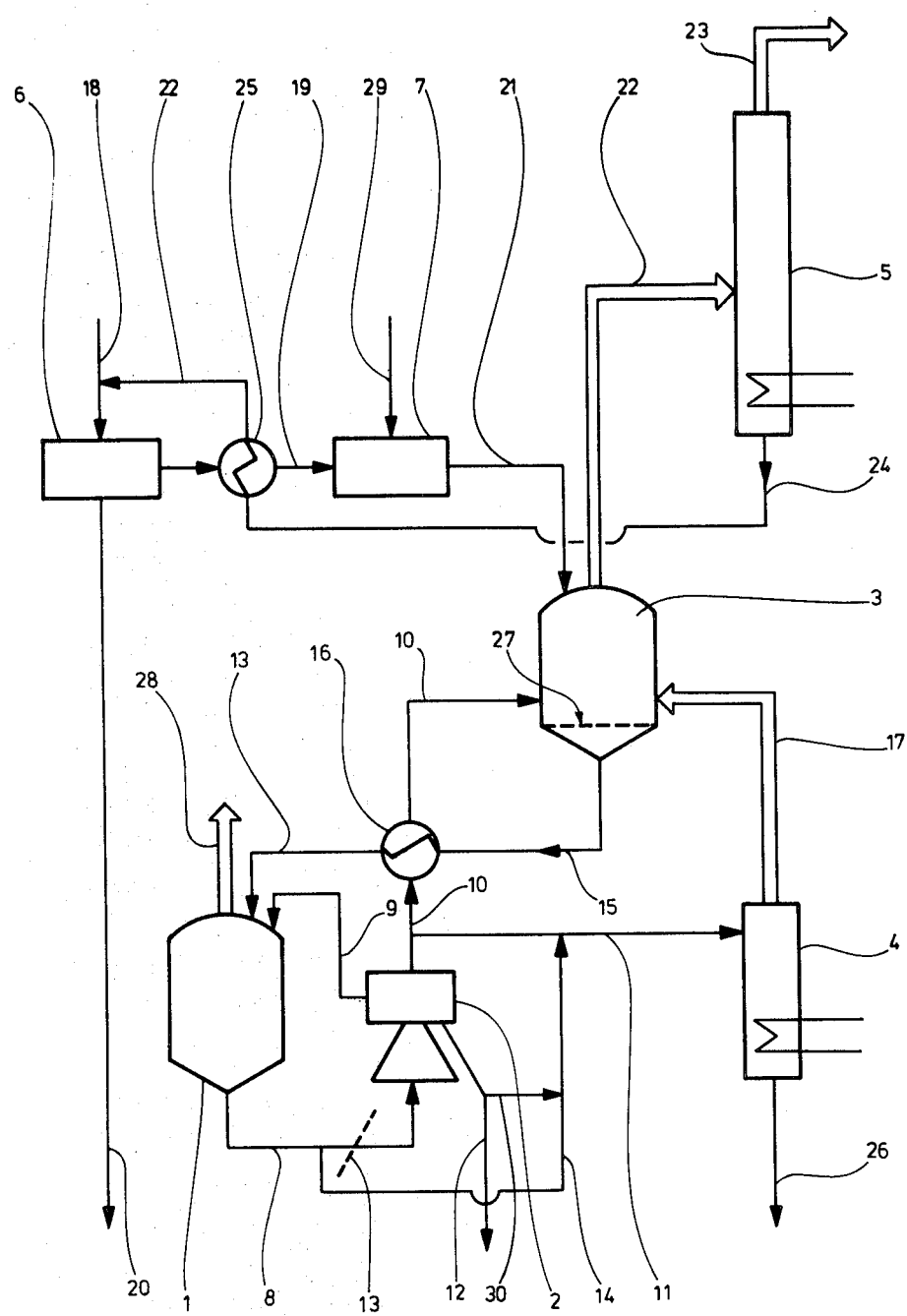

PROCESS FOR PRODUCING ETHANOL BY CONTINUOUS FERMENTATION OF POLYSACCHARIDE-CONTAINING RAW MATERIALS

This invention relates to a process for producing ethanol by continuous fermentation of polysaccharide-containing raw materials, the fermentation being carried out in one or several fermentors, a stream of fermentation liquor being separated into one yeast concentrate stream and one yeast-free flow and also possibly a sludge stream, of which the yeast concentrate flow is recirculated to the fermentor, at least part of the yeast-free stream being fed to a simple evaporator unit, corresponding to one or a few distilling stages, wherein it is separated *partly* into a first vapour stream, enriched in ethanol, which is fed to a plant for production of the desired ethanol grade, and *partly* into a first liquid bottom stream, which is at least in part recirculated to the fermentor.

Such a method is disclosed in the Swedish Patent Application No. 7901738-0. It is provided, that the raw material stream to the fermentor consists of directly fermentable, i.e. saccharified carbohydrates.

In conventional fermentation, carried out batch-wise, it is also known to add, after boiling (gelatinization) of starch-containing raw materials, malt or enzymes, carrying out the saccharifying in the fermentor. This is only feasible practically, however, when there is ample of time for the process. The saccharifying and the fermentation will require about the same time, namely 40-50 hours. In order to reduce this time substantially, uneconomically large amounts of enzymes and yeast would be required at the fermentation temperature. The saccharifying enzymes are soluble and cannot, from a practical economical point of view, be recovered. Also, the enzyme reactions have to be carried out at higher temperatures than the fermentation in order that the saccharifying time shall be substantially reduced. In methods utilized until now for rapid fermentation and continuous methods, it has been necessary to perform the saccharifying separately under optimal conditions. The drawback of such a mode of operation is a high capital cost and energy consumption and above all, inhibition by the monosaccharides formed of the saccharifying, i.e. the enzymatic hydrolysis. Furthermore, di- and trisaccharides are reformed from glucose at prolonged reaction time if the glucose concentration is high.

The object of the present invention is to provide a method initially mentioned in which these drawbacks have been eliminated. According to the invention, a method of the type initially mentioned is characterized in that a raw material stream is fed to a circulation circuit, comprising said fermentor and said simple evaporator unit.

It is advantageous to separate a stream of fermentation liquor from the fermentor into a yeast concentrate stream and yeast-free flow and possibly a sludge stream by a centrifugal separator.

According to one suitable embodiment of the new method, the polysaccharide-containing raw materials are firstly gelatinized (liquefied) to a prehydrolysate, which can mean different stages of break down, such as dextrines, oligosaccharides etc., whereupon said prehydrolysate is hydrolysed further enzymatically in the evaporator unit to fermentable sugar. The enzymes utilized for further hydrolysis of the prehydrolysate are suitably added separately to the evaporator unit of fermentor. The saccharifying reaction in the evaporation unit is carried out at a temperature, where the enzymes utilized are active, and at which the ethanol can be driven off without using too low a pressure, i.e. preferably within the temperature range 35° C.-75° C.

The starch is gelatinized, i.e. is liquefied by boiling, and in order to reduce the viscosity there is usually added a thermostable alpha-amylase. Further hydrolysis, i.e. the sacharifying, is suitably carried out by means of a gluco-amylase, if the raw material is starch, and a cellulase, if the raw material is cellulose. If a mixture of starch and cellulose is used as raw material, the hydrolysis can be carried out simultaneously by means of starch- and cellulose down-breaking enzymes.

Considering the different extent of break down in different parts of the raw material, that enters the evaporator unit in a prehydrolysed state, which means, that there may be present more or less solid particles, it is advantageous to keep these in the evaporator unit by means of a sieve means, in order that their retention time is prolonged, resulting in break down and hydrolysis. It is advantageous to carry out the new method so that part of the yeast-free stream from the centrifugal separation is fed to a stripping unit, in which this portion of the yeast-free stream is separated, *partly* into a second vapour stream, enriched in ethanol, and *partly* into a second liquid bottom flow, exhausted in ethanol.

The discharge of impurities, like fibres, protein aggregates etc. can be arranged in different ways. According to one suitable embodiment of the method, the flow of fermentation liquid from the fermentor is brought to pass a second sieve means, a stream containing fine fibres and agglomerated protein particles separated by the sieve means being discharged from the flow of fermentation liquid. Suitably this stream of particles is fed to said stripping unit. Thus the yeast cells will pass said second sieve means and are separated by the centrifugal separator.

It is also advantageous to separate a stream of fermentation liquid, not only into a yeast concentrate stream and a yeast-free flow, but also into a stream of impurities like dead yeast cells and other solid impurities, which stream is suitably fed, at least in part, to said stripping unit. This separation can be carried out intermittently by centrifugal separation. From a heat economy point of view it is advantageous to transfer heat to the raw material stream, entering the evaporation unit, from a bottom stream, discharged from the plant for production of the desired ethanol grade.

The method of the invention will now be described more in detail, reference being made to the accompanying drawing, which shows schematically, a flow sheet of a plant for carrying out the method of the invention.

In the drawing, 1 is a fermentor, 2 a centrifugal separator, 3 an evaporation unit, which also acts as a hydrolysis reactor, 4 a stripping unit and 5 a fractionating column for production of the desired ethanol grade. The plant also comprises a unit 6 for substrate pretreatment and a unit 7 for prehydrolysis. The fermentor 1 is a connected, via a line 8 to the centrifugal separator 2, which is provided to separate the incoming feed of fermentation liquor *partly* into a yeast concentrate stream, which is recirculated to the fermentor via a line 9, *partly* into a yeast-free stream, which is fed, via a line 10 to the evaporation unit 3, and into a smaller part-stream, by bifurcation from the line 10 to a line 11, which is connected to the stripping unit 4, and finally *partly* into an intermediate sludge stream of more or less solid impurifies, which stream is discharged via a line 12. There is provided a sieve means 13 in line 8 in this plant, separating particles larger than yeast cells, for instance 100μ. These particles are conveyed, as a stream via a line 14 and line 11 to the stripping unit 4. Sludge steam 12 from the centrifugal separator can also be fed into the stripping unit 4. A flow is conveyed from the evaporation unit 3 via a line 15 back to the fermentor 1, a heat exchanger 16 being provided to transfer heat from the flow in the line 15 to the stream in the line 10. This simply means, that the temperature in the fermentor 1 is kept at normal fermentation temperature, i.e. about 32° C., while the temperature in the evaporation unit is kept considerably higher, according to the invention preferably within the range 35° C.–75° C. A vapour stream, enriched in ethanol is conveyed from the stripping unit 4 via a line 17 to the evaporation unit 3. The raw material is fed via a line 18 to the unit 6 for pretreatment of the substrate, which is connected, *partly* to a line 19 to the unit for prehydrolysis 7, and *partly* to a line 20, by which the main part of non-soluble, non-fermentable material is discharged from the plant. The unit for prehydrolysis 7 is connected to the evaporation unit 3 via a line 21. A vapour stream, enriched in ethanol is conveyed via a line 22 to the fractionating column 5, from which there is discharged, *partly* an ethanol stream via a line 23, and *partly* a liquid bottom stream, which is fed, via a line 24 to the unit for pretreatment of substrate 6. A heat exchanger 25 is provided to transfer heat from said bottom stream to the stream of raw material in the line 19. The stripping unit 4, the fractionating column 5 and the evaporator unit 3 are provided with heating surfaces, for instance in the form of pipe coils for indirect heat transfer. The stripping unit 4 is provided with a bottom outlet 26. Considering the temperature in the evaporator unit, 35° C. to 75° C., a corresponding vacuum is maintained in the same by means, which is not shown. Furthermore there are provided in the plant pumps if necessary to maintain streams and to overcome pressure differences. The evaporator unit can be provided with a sieve means 27, which prevents more or less solid particles, which have not been digested, from reaching the fermentor. The fermentor is provided with an outlet 28 for the carbon dioxide formed. An intake 29 for steam is provided on the unit for prehydrolysis 7.

EXAMPLE: Starch-containing raw material-wheat

If the raw material contains starch, such as grain or rootcrops, it is preferably ground, and non-soluble matters, which cannot be broken down to fermentable sugar are separated and are usually dried to fodder together with the slop from the distilling plant for production of the desired ethanol grade. In the plant shown in the drawing, the raw material is separated in the unit 6 by conventional means, not shown, into a stream of such non-soluble matters, which is discharged via the line 20, and a stream of starch suspension, which is fed to the unit for prehydrolysis as a relatively concentrated suspension, i.e. with a limited amount of water added considering the energy consumption in the plant, so that the starch concentration in the suspension is preferably more than 40% (weight). The starch suspension is preheated to about 65° C. in the heat exchanger 25, and a thermostable alpha-amylase, like NOVO TERMAMYL 60 L is added. The starch suspension is pumped continuously through the unit 7 for prehydrolysis, which is formed like a tube reactor. 3.7 parts steam are added per part of suspension, and the temperature rises to about 105° C. The residence time in the tube reactor is about 5 minutes, whereby the starch is gelatinized, i.e. is liquefied, before it is allowed to expand into the evaporator unit 3, where a vacuum corresponding to a temperature of 65° C. is maintained. The prehydrolysis can alternatively be carried out at lower temperature (ca 90° C.) and kept longer time (ca 2 hours) before entering the circulation circuit.

As is obvious from the description of the plant a stream is circulated between the evaporator unit 3 and the fermentor 1. The evaporator unit and the fermentor have about the same volume in this plant, and the residence time in them is totally about 8 hours (divided as about 4 hours in the evaporator unit and 4 hours in the fermentor). Of course the reaction time needed varies with the temperature and the concentration of added enzyme. In the present example saccharifying enzymes, i.e. enzymes for further hydrolysis of prehydrolysed starch to fermentable sugar, is added in the form of NOVO gluco-amylase SAN 150 L at the start of the process as well in the evaporator unit 3, i.e. the saccharifying reactor, and in the fermentor 1, in which there is maintained a temperature of 32° C. The prehydrolysed starch is saccharified, and the sugar formed is fermented by baker's yeast (*Saccharomyces cerevisiae*) in the fermentor. The yeast is separated continuously from the stream in the line 8 by the centrifugal separator 2 and is recirculated via the line 9 in the form of a yeast concentrate, to the fermentor 1.

The yeast-free stream is pumped to the evaporator unit 3, where a vapour stream, enriched in ethanol, is driven off simultaneously with the saccharifying of prehydrolysed starch fed to the fermentor and recirculated, via the heat exchanger 16 to the fermentor 1. The enzymes are not consumed, but are recirculated, and from an economical point of view, high enzyme concentrations are permissible. Only the amounts of enzymes, which are lost with the bottom stream of slop from the stripping unit 4 through the bottom outlet 26 must be replaced. A certain addition due to an inactivation of the enzymes with time is needed. By means of this last mentioned stream the material balance is maintained in the system, in order that the concentration of soluble, non-fermentable matter does not rise above about 15% in the fermentor 1.

The following composition of the in- and outgoing stream is obtained in the present example: (Chemicals for nutrition and pH-control have been omitted.)

TABLE 1

| Starch-containing raw material | | | | | |
|---|---|---|---|---|---|
| Flow (see the drawing) | (19) | (29) | (22) | (26) | (28) |
| starch | 47.25 | | | | |
| ethanol | | | 21.70 | | 0.20 |
| sugar | | | | 0.85 | |
| glycerol | | | | 1.80 | |
| $CO_2$ | | | | | 20.80 |
| steam | | 3.70 | | | |
| water | 50.00 | | 50.70 | 3.00 | |
| non solub./non fermentab. | 1.75 | | | 1.75 | |
| soluble/non fermentable | 1.00 | | | 1.00 | |
| other matter | | | | 0.60 | 1.30 |
| SUM | 100.00 | 3.70 | 73.00 | 9.70 | 21.00 |

Raw material cellulose

It is more difficult to saccharify cellulose than starch. This is particularly true if the crystaline ligno-cellulose is considered. It is thus important to choose the proper pretreatment. Lignin and other non-fermentable matter must be separated and discharged, as they can act inhibiting on the fermentation process. The fibres should be freed in order to give the enzymes a large surface for attack.

Several pretreatment methods are possible, according to the type of raw material. If wooden chips, straw etc. is the raw material, a thermal disruption is suitable. Thereupon an acid prehydrolysis at high temperature and short contact time in order to prevent the reforming of non fermentable sugars is carried out, the pentoses being separated and discharged from the process. If the pentoses are not discharged they will be found in the slop from the process and can be worked up to furfural, fodder yeast etc.

The prehydrolysed cellulose material is fed, in the same way as described in the example above with starch raw material, to the evaporator unit 3. In the reaction system, i.e. the circuit comprising the evaporator unit 3 and the fermentor 1, there is maintained a high concentration of a suitable enzyme system, for instance a mixture of cellulase and cellobiase, and an optimal temperature considering the enzyme activity and the driving off of ethanol in the evaporator unit 3. The reaction time for hydrolysis of prehydrolysed cellulose is longer than for prehydrolysed starch, which means, that the capacity of the plant will be reduced accordingly. Usually the raw material contains high concentrations of soluble, non fermentable material, which means, that the stream to the stripping unit will be large, accordingly.

Raw material starch and cellulose

Most raw materials containing starch, especially root crops like cassava and potatoe contain large portions of cellulose fibres after pretreatment, which fibres are difficult to separate. These fibres are thin and are easily hydrolysable. Thus it is suitable to let them join the starch suspension, that is fed to the evaporator unit 3, i.e. the saccharifying reactor. In order to hydrolyse this mixture a mixture of enzymes is needed, i.e. amylases and cellulases. These enzymes do no show the same optimal temperature of activity, which means, that a compromise has to be applied, in order to get the best possible yield of sugar/ethanol.

I claim:

1. A process for making ethanol which comprises adding a fermentable feed substance to a fermentor, fermenting said feed substance, continuously withdrawing fermentation liquor from said fermentor, continuously dividing said withdrawn fermentation liquor into a yeast-concentrate stream and a yeast-free stream, continuously recirculating said yeast-concentrate steam to the fermentor, continously passing the yeast-free stream to the separator, feeding to said separator polysaccharides and at least one hydrolytic enzyme, separating the yeast-free stream into a first ethanol enriched vapor phase and a first liquid bottoms stream, feeding said first ethanol enriched vapor phase to an ethanol recovery plant, conducting the separation of the ethanol enriched vapor phase from the yeast-free stream in the separator under a temperature higher than the fermentation temperature and under conditions suitable for enzymatic hydrolysis, whereby, during the separation of said yeast-free stream, the polysaccharides are hydrolysed by the action of at least one hydrolytic enzyme to fermentable saccharides, and recirculating part of said first bottoms stream containing said fermentable saccharides to the fermentor.

2. The process of claim 1 wherein part of said yeast-free stream is fed to a stripping unit where it is separated into a second vapor phase enriched in ethanol and into a third liquid bottom stream exhausted of ethanol.

3. The process of claim 1, in which said fermentation liquor is separated in a centrifugal separator.

4. The process claimed in claim 1, in which the part of the first liquid bottoms stream recirculated to the fermentor is sieved to remove undigested particles.

5. The process claimed in claim 1 wherein the fermentation liquor drawn from the fermentor is sieved to remove particles.

6. The process of claim 5, in which in that the stream containing particles separated by a sieve means is fed to a stripping unit.

7. The process claimed in claim 1 comprising separating the withdrawn fermentation liquor into a yeast concentrate stream, a yeast-free stream and a sludge stream of impurities.

8. The process of claim 7, in which at least part of said sludge stream is fed to a stripping unit.

9. The process claimed in claim 1 wherein the ethanol recovery plant contains a fractionating unit generating a second bottoms stream and transferring heat from said second bottoms stream to the polysaccharide containing feed stream.

10. The process claimed in claim 1 in which the polysaccharide is first liquified to a prehydrolysate before adding the polysaccharide to the yeast-free stream and said prehydrolysate is further hydrolysed to a fermentable state by enzymes during ethanol separation of said yeast-free stream.

11. The process claimed in claim 10 wherein the enzymes which further hydrolyse the prehydrolysate are fed to the fermentor or the separator.

12. The process of claim 10 in which the further hydrolysis in the separator is carried out at a temperature within the range 35° C.–75° C.

13. The process of claim 10, in which the further hydrolysis is carried out by means of a glucoamylase.

14. The process of claim 10, in which the further hydrolysis is carried out by means of a cellulase.

15. The process of claim 10, in which the further hydrolysis is carried out simultaneously with enzymes breaking down starch and enzymes breaking down cellulose.

* * * * *